United States Patent
Djupesland et al.

(10) Patent No.: US 9,452,272 B2
(45) Date of Patent: Sep. 27, 2016

(54) DELIVERY DEVICES

(75) Inventors: Per Gisle Djupesland, Oslo (NO); Martin Joseph Murphy, Letchworth Garden (GB); Stuart Brian William Kay, Melbourn (GB); Andrew Gordon Pocock, Royston (GB)

(73) Assignee: OptiNose AS, Oslo (NO)

(*) Notice: Subject to any disclaimer, the term of this patent is extended or adjusted under 35 U.S.C. 154(b) by 331 days.

(21) Appl. No.: 13/473,277

(22) Filed: May 16, 2012

(65) Prior Publication Data

US 2013/0125889 A1    May 23, 2013

Related U.S. Application Data

(63) Continuation of application No. 12/871,443, filed on Aug. 30, 2010, now abandoned, which is a continuation of application No. 10/568,391, filed as application No. PCT/IB2004/002751 on Aug. 16, 2004, now Pat. No. 7,784,460.

(30) Foreign Application Priority Data

Aug. 14, 2003 (GB) .................................. 0319119.4

(51) Int. Cl.
*A61M 15/00* (2006.01)
*A61M 11/02* (2006.01)
*A61M 15/08* (2006.01)

(52) U.S. Cl.
CPC .......... *A61M 15/0091* (2013.01); *A61M 11/02* (2013.01); *A61M 15/00* (2013.01); *A61M 15/0098* (2014.02); *A61M 15/08* (2013.01)

(58) Field of Classification Search
CPC ............. A61M 11/00; A61M 11/006; A61M 11/007; A61M 11/008; A61M 15/00; A61M 15/0001; A61M 15/002; A61M 15/0021; A61M 15/0028; A61M 15/003; A61M 15/0033; A61M 15/0035; A61M 15/0038; A61M 15/004; A61M 15/0041; A61M 15/0091; A61M 15/0098; A61M 13/00
USPC ............ 128/203.15, 200.14, 203.12, 203.18, 128/203.14, 203.13, 203.19, 203.21, 203.23
See application file for complete search history.

(56) References Cited

U.S. PATENT DOCUMENTS 605,436 A    6/1898    Kellogg
642,748 A    2/1900    Manners (Continued)

FOREIGN PATENT DOCUMENTS

EP    1 008 361    6/2000
FR    2 597 331    10/1987

(Continued)

OTHER PUBLICATIONS

International Search Report for International App. No. PCT/IB04/002751 (7 pages).

(Continued)

*Primary Examiner* — Tatyana Zalukaeva
*Assistant Examiner* — Colin W Stuart
(74) *Attorney, Agent, or Firm* — Finnegan, Henderson, Farabow, Garrett & Dunner, LLP

(57) ABSTRACT

A breath-actuated delivery device includes a mouthpiece through which a subject in use exhales, an air channel which is in fluid communication with the mouthpiece, and a flexible diaphragm which is disposed in the air channel. The diaphragm provides for at least a restricted air flow through the air channel until a predeterminable actuation pressure is developed in the mouthpiece, and, on generation of the predeterminable actuation pressure in the mouthpiece, provides for an air flow through the air channel.

18 Claims, 17 Drawing Sheets

(56) References Cited

U.S. PATENT DOCUMENTS

| | | | |
|---|---|---|---|
| 746,749 A | 12/1903 | Seidel | |
| 5,020,529 A * | 6/1991 | Gobin | 128/202.28 |
| 5,113,855 A | 5/1992 | Newhouse | |
| 5,657,746 A * | 8/1997 | Christianson | 128/201.11 |
| 5,738,087 A | 4/1998 | King | |
| 5,797,392 A | 8/1998 | Keldmann et al. | |
| 6,648,848 B1 | 11/2003 | Keldmann et al. | |
| 6,679,253 B1 | 1/2004 | Feng | |
| 6,715,485 B1 | 4/2004 | Djupesland | |
| 6,962,151 B1 | 11/2005 | Knoch et al. | |
| D530,815 S | 10/2006 | Murphy et al. | |
| 7,347,201 B2 | 3/2008 | Djupesland | |
| 7,377,901 B2 | 5/2008 | Djupesland et al. | |
| 7,481,218 B2 | 1/2009 | Djupesland | |
| 7,543,581 B2 | 6/2009 | Djupesland | |
| 7,740,014 B2 | 6/2010 | Djupesland | |
| 7,784,460 B2 | 8/2010 | Djupesland et al. | |
| 7,841,337 B2 | 11/2010 | Djupesland | |
| 7,854,227 B2 | 12/2010 | Djupesland | |
| 7,934,503 B2 | 5/2011 | Djupesland et al. | |
| 7,975,690 B2 | 7/2011 | Djupesland | |
| 8,047,202 B2 | 11/2011 | Djupesland | |
| 8,146,589 B2 | 4/2012 | Djupesland | |
| 8,171,929 B2 | 5/2012 | Djupesland et al. | |
| 8,327,844 B2 | 12/2012 | Djupesland | |
| 8,511,303 B2 | 8/2013 | Djupesland | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,590,530 B2 | 11/2013 | Djupesland et al. | |
| 8,596,278 B2 | 12/2013 | Djupesland | |
| 8,800,555 B2 | 8/2014 | Djupesland | |
| 8,875,704 B2 | 11/2014 | Djupesland et al. | |
| 8,899,229 B2 | 12/2014 | Djupesland et al. | |
| 8,910,629 B2 | 12/2014 | Djupesland et al. | |
| D723,156 S | 2/2015 | Djupesland et al. | |
| D725,769 S | 3/2015 | Djupesland et al. | |
| 8,978,647 B2 | 3/2015 | Djupesland et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |
| 9,072,857 B2 | 7/2015 | Djupesland | |
| 9,108,015 B2 | 8/2015 | Djupesland | |
| 9,119,932 B2 | 9/2015 | Djupesland | |
| 9,132,249 B2 | 9/2015 | Djupesland | |
| 9,144,652 B2 | 9/2015 | Djupesland et al. | |
| 9,168,341 B2 | 10/2015 | Djupesland | |
| 9,205,208 B2 | 12/2015 | Djupesland | |
| 9,205,209 B2 | 12/2015 | Djupesland | |
| 9,272,104 B2 | 3/2016 | Djupesland | |
| 2001/0015387 A1 | 8/2001 | Fuchs | |
| 2002/0157664 A1 | 10/2002 | Fugelsang et al. | |
| 2003/0079743 A1 | 5/2003 | Genova et al. | |
| 2004/0024330 A1 | 2/2004 | Djupesland et al. | |
| 2004/0079362 A1 | 4/2004 | Christrup et al. | |
| 2004/0112378 A1 | 6/2004 | Djupesland | |
| 2004/0112379 A1 | 6/2004 | Djupesland | |
| 2004/0112380 A1 | 6/2004 | Djupesland | |
| 2004/0149289 A1 | 8/2004 | Djupesland | |
| 2004/0182388 A1 | 9/2004 | Djupesland | |
| 2005/0028812 A1 | 2/2005 | Djupesland | |
| 2005/0072430 A1 | 4/2005 | Djupesland | |
| 2005/0235992 A1 | 10/2005 | Djupesland | |
| 2006/0096589 A1 | 5/2006 | Djupesland | |
| 2006/0107957 A1 | 5/2006 | Djupesland | |
| 2006/0169278 A1 | 8/2006 | Djupesland et al. | |
| 2006/0219240 A1 | 10/2006 | Djupesland | |
| 2006/0219241 A1 | 10/2006 | Djupesland | |
| 2006/0225732 A1 | 10/2006 | Djupesland | |
| 2006/0231094 A1 | 10/2006 | Djupesland | |
| 2007/0039614 A1 | 2/2007 | Djupesland | |
| 2007/0125371 A1 | 6/2007 | Djupesland | |
| 2007/0186927 A1 | 8/2007 | Djupesland et al. | |
| 2008/0161771 A1 | 7/2008 | Djupesland | |
| 2008/0163874 A1 | 7/2008 | Djupesland | |
| 2008/0221471 A1 | 9/2008 | Djupesland et al. | |
| 2008/0223363 A1 | 9/2008 | Djupesland | |
| 2008/0289629 A1 | 11/2008 | Djupesland et al. | |
| 2009/0101146 A1 | 4/2009 | Djupesland | |
| 2009/0293873 A1 | 12/2009 | Djupesland et al. | |
| 2009/0304802 A1 | 12/2009 | Djupesland et al. | |
| 2009/0314293 A1 | 12/2009 | Djupesland | |
| 2009/0320832 A1 | 12/2009 | Djupestand | |
| 2010/0035805 A1 | 2/2010 | Hafner | |
| 2010/0051022 A1 | 3/2010 | Djupesland et al. | |
| 2010/0057047 A1 | 3/2010 | Djupesland et al. | |
| 2010/0242959 A1 | 9/2010 | Djupesland et al. | |
| 2010/0282246 A1 | 11/2010 | Djupesland et al. | |
| 2010/0288275 A1 | 11/2010 | Djupesland et al. | |
| 2010/0300439 A1 | 12/2010 | Djupesland et al. | |
| 2011/0023869 A1 | 2/2011 | Djupesland | |
| 2011/0053827 A1 | 3/2011 | Hafner | |
| 2011/0088690 A1 | 4/2011 | Djupesland et al. | |
| 2011/0088691 A1 | 4/2011 | Djupesland | |
| 2011/0114087 A1 | 5/2011 | Djupesland et al. | |
| 2011/0126830 A1 | 6/2011 | Djupesland et al. | |
| 2011/0259329 A1 | 10/2011 | Djupesland et al. | |
| 2011/0318345 A1 | 12/2011 | Djupesland | |
| 2012/0000459 A1 | 1/2012 | Djupesland | |
| 2012/0006323 A1 | 1/2012 | Djupesland | |
| 2012/0073571 A1 | 3/2012 | Djupesland | |
| 2012/0090608 A1 | 4/2012 | Djupesland et al. | |
| 2012/0260915 A1 | 10/2012 | Djupesland | |
| 2013/0098362 A1 | 4/2013 | Djupesland et al. | |
| 2013/0125889 A1 | 5/2013 | Djupesland et al. | |
| 2013/0327320 A1 | 12/2013 | Djupesland | |
| 2014/0018295 A1 | 1/2014 | Djupesland | |
| 2014/0041660 A1 | 2/2014 | Djupesland et al. | |
| 2014/0060536 A1 | 3/2014 | Djupesland | |
| 2014/0073562 A1 | 3/2014 | Djupesland | |
| 2014/0144442 A1 | 5/2014 | Djupesland et al. | |
| 2014/0144443 A1 | 5/2014 | Djupesland et al. | |
| 2014/0166008 A1 | 6/2014 | Djupesland | |
| 2014/0202456 A1 | 7/2014 | Djupesland | |
| 2014/0246022 A1 | 9/2014 | Djupesland et al. | |
| 2015/0007811 A1 | 1/2015 | Djupesland et al. | |
| 2015/0013670 A1 | 1/2015 | Djupesland et al. | |
| 2015/0013677 A1 | 1/2015 | Djupesland et al. | |
| 2015/0053201 A1 | 2/2015 | Djupesland et al. | |
| 2015/0090259 A1 | 4/2015 | Djupesland et al. | |
| 2015/0101605 A1 | 4/2015 | Djupesland et al. | |
| 2015/0144129 A1 | 5/2015 | Djupesland et al. | |
| 2015/0182709 A1 | 7/2015 | Djupesland | |
| 2015/0246194 A1 | 9/2015 | Djupesland et al. | |
| 2015/0367090 A1 | 12/2015 | Djupesland et al. | |
| 2015/0367091 A1 | 12/2015 | Djupesland et al. | |
| 2016/0001022 A1 | 1/2016 | Djupesland et al. | |
| 2016/0045687 A1 | 2/2016 | Djupesland | |
| 2016/0051778 A1 | 2/2016 | Djupesland et al. | |
| 2016/0074603 A1 | 3/2016 | Djupesland et al. | |
| 2016/0082206 A1 | 3/2016 | Djupesland et al. | |
| 2016/0082207 A1 | 3/2016 | Djupesland et al. | |

FOREIGN PATENT DOCUMENTS

| | | |
|---|---|---|
| GB | 2 367 756 | 4/2002 |
| WO | 92/21404 | 12/1992 |
| WO | WO 96/22802 | 8/1996 |
| WO | WO 98/53869 | 12/1998 |
| WO | 00/51672 | 9/2000 |
| WO | WO 00/51672 | 9/2000 |
| WO | WO 01/97689 | 12/2001 |
| WO | 02/068029 | 9/2002 |
| WO | 02/068030 | 9/2002 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | 03/000329 | 1/2003 |
| WO | WO 03/000310 | 1/2003 |
| WO | 03/020350 | 3/2003 |
| WO | WO 03/020350 | 3/2003 |
| WO | WO 03/082393 | 10/2003 |

(56) References Cited

FOREIGN PATENT DOCUMENTS

| | | |
|---|---|---|
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered with a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).

\* cited by examiner

DELIVERY DEVICES

CROSS REFERENCE TO RELATED APPLICATIONS

This application is a continuation of U.S. patent application Ser. No. 12/871,443, filed Aug. 30, 2010, which is a continuation of U.S. patent application Ser. No. 10/568,391, filed Dec. 21, 2006, which is a National Phase Application of International Application No. PCT/IB2004/002751, filed on Aug. 16, 2004, which claims the benefit of and priority to UK patent application no. GB 0319119.4, filed on Aug. 14, 2003. The disclosures of the above applications are incorporated herein by reference in their entireties.

FIELD OF THE INVENTION

The present invention relates to a delivery device, in particular a breathactuated nasal delivery device, for and a method of delivering substance, in particular one of a liquid, as a suspension or solution, or a powder containing a medicament, especially systemic or topical pharmaceuticals, or a vaccine to the nasal airway of a subject.

BACKGROUND

Referring to FIG. 8, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

SUMMARY OF THE INVENTION

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, antiemetics, insulin, anti-epileptics, sedatives and hypnotica, and other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practiced to remove particles and secretions, as well as to improve the mucociliary activity of the nasal mucosa. These solutions can be used in combination with active pharmaceuticals.

To date, nasal medicaments have been primarily delivered as drops or by mechanical nasal spray pumps. With mechanical spray pumps, the mean particle size is typically between 40 µm and 80 µm in order to prevent the inhalation of delivered particles. In general, particles smaller than 10 µm will bypass the nose and can be inhaled. Indeed, the new FDA guidelines require that the fraction of particles less than 10 µm be at most 5%.

Whilst the provision of a spray having a larger mean particle size prevents the inhalation of the particles, these larger particles are not optimal for achieving a good distribution to the nasal mucosa.

The applicant has now recognized that the closure of the oropharyngeal velum during the delivery of a substance to the nasal airway prevents the possible inhalation of the substance, thereby enabling the delivery of an aerosol having a much smaller mean particle size than achieved by traditional nasal spray pumps. In this way, an aerosol can be generated which has an optimal particle size distribution.

In addition, the applicant has recognized that, by establishing a bidirectional flow through the nasal cavities as described in WO-A-00/51672, that is, an air flow which passes into one nostril, around the posterior margin of the nasal septum and in the opposite direction out of the other nostril, an aerosol having an optimal flow rate and timing can be generated. Furthermore, the bi-directional air flow advantageously acts to stimulate the sensory nerves in the nasal mucosa, thereby conditioning the subject for the delivery and providing a more comfortable delivery situation.

A yet further advantage is that the air flow acts to create a positive pressure inside the nasal passages connected in series, which tends to expand and widen narrow and congested regions.

A still yet further advantage is that the two-point fixation of the device in the nose with a well-fitting nozzle and in the mouth provides a much more stable and reproducible positioning of the device as compared to traditional spray pumps. Thus, in addition to improved deposition and reproducibility, the new concept provides a more user-friendly and intuitive nasal delivery method.

Furthermore, a delivery device, in being pre-primed and actuatable by the oral exhalation breath of a subject, does not require the application of an actuation force by the subject at the time of actuation. Traditionally, mechanical liquid delivery pumps are operated by the manual compression of a chamber containing a volume of liquid to expel a flow of a metered volume of liquid, and mechanical powder delivery pumps are operated by the manual compression of a chamber containing a volume of air to drive and expel a flow of a metered amount of a dry powder. Such operation requires a relatively high actuation force, typically of the order of 50 N, which high force often leads to significant movement of the delivery device, it being very difficult to maintain a delivery device stationary when attempting to apply a high actuation force. Movement of the delivery device, both in the positioning and orientation of the nozzle, will lead to poor reproducibility, dose accuracy and patient compliance. In being pre-primed and actuatable by the oral exhalation breath of a subject, the delivery device of the present invention overcomes this problem.

In addition, by not requiring a subject to apply an actuation force at the instance of delivery, the delivery device provides for the same actuation force in each delivery, and also provides for delivery at an optimal pressure and/or flow rate, and the delivery of substance having an optimized particle size distribution.

Yet furthermore, in providing for the closure of the oropharyngeal velum of a subject, substance is prevented from entering the lower airway, and also, in a preferred embodiment, bi-directional delivery can be achieved through the nasal cavities.

In one aspect the present invention provides a breath-actuated delivery device, comprising: a delivery unit actuatable to deliver substance on application of a delivery force thereto; a loading unit actuatable to apply the delivery force to the delivery unit to actuate the same; a mouthpiece through which a subject in use exhales; an air channel in fluid communication with the mouthpiece; and an actuating member disposed in the air channel, the actuating member comprising a flexible, bi-stable element actuatable, on exhalation by the subject into the mouthpiece, between a first, non-actuated state and a second, actuated state in which the actuating member actuates the loading unit to apply the delivery force to the delivery unit to actuate the same.

In another aspect the present invention provides a delivery device, comprising: a delivery unit actuatable to deliver substance on application of a delivery force thereto; and a loading unit actuatable to apply the delivery force to the delivery unit to actuate the same, the loading unit comprising a drive member actuatable from a loaded position to actuate the delivery unit, a biasing element for loading the drive member with the delivery force, and a restraining member for normally restraining the drive member in the loaded position and being configured to be broken on actuation of the loading unit to release the drive member and cause the biasing element to drive the drive member to actuate the delivery unit.

In a further aspect the present invention provides a breath-actuated delivery device, comprising: a mouthpiece through which a subject in use exhales; an air channel in fluid communication with the mouthpiece; and a flexible diaphragm disposed in the air channel, the diaphragm providing for at least a restricted air flow through the air channel until a predeterminable actuation pressure is developed in the mouthpiece, and, on generation of the predeterminable actuation pressure in the mouthpiece, providing for an air flow through the air channel.

In a yet further aspect the present invention provides a delivery device, comprising: a delivery unit actuatable to deliver substance on application of a delivery force thereto; and a loading unit actuatable to apply the delivery force to the delivery unit to actuate the same.

In a still further aspect the present invention provides a method of delivering substance to a nasal airway of a subject, the method comprising the steps of: providing a delivery unit actuatable to deliver substance on application of a delivery force thereto; loading a loading unit with the delivery force; and actuating the loading unit to apply the delivery force to the delivery unit to actuate the same.

BRIEF DESCRIPTION OF THE DRAWINGS

Preferred embodiments of the present invention will now be described hereinbelow by way of example only with reference to the accompanying drawings, in which.

DETAILED DESCRIPTION

Figure 1:
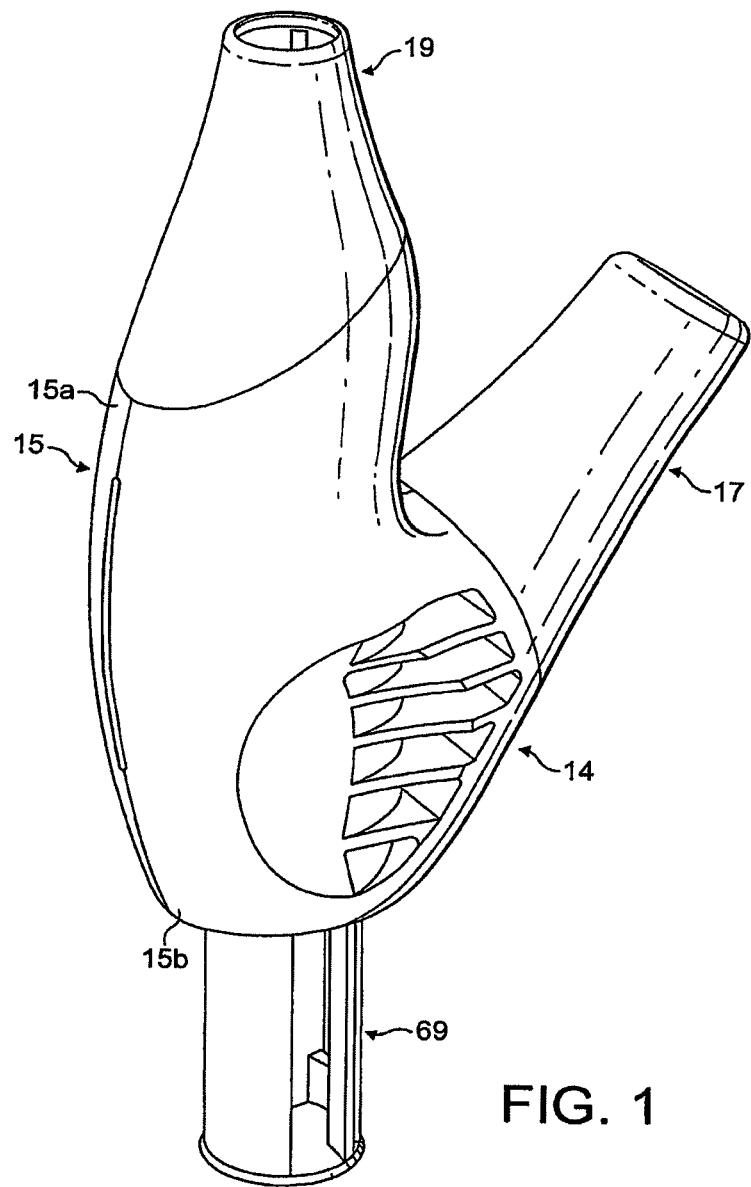
FIG. 1 illustrates a perspective view of a nasal delivery device in accordance with a first embodiment of the present invention.
Figure 2:
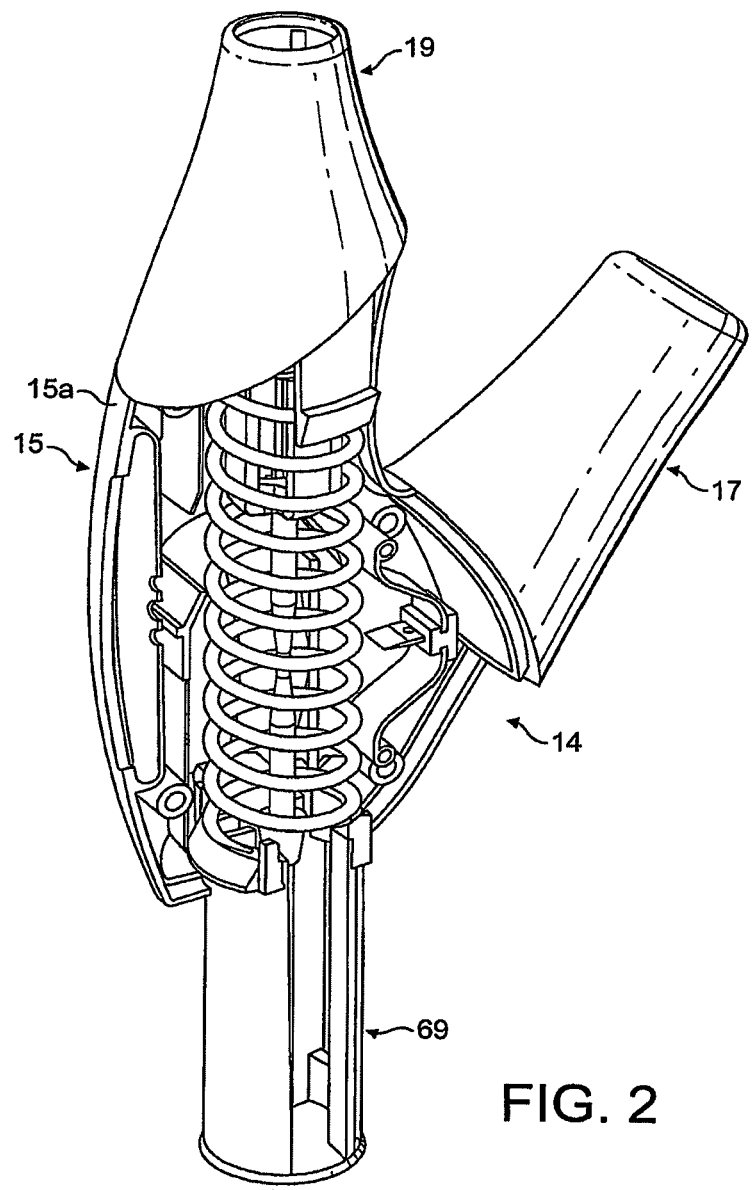
FIG. 2 illustrates a part cut-away perspective view of the delivery device of FIG. 1.

FIGS. 1 to 3 illustrate a breath-actuated nasal delivery device in accordance with a first embodiment of the present invention.

The delivery device comprises a body unit 14 which comprises a housing 15, in this embodiment provided by first and second housing parts 15a, 15b, which is typically gripped in the hand of a user, a mouthpiece 17 through which the user exhales to actuate the delivery device, and a nosepiece 19 for fitting to a nostril of the user and through which substance is delivered to the nasal airway of the user.

The housing 15 includes a cavity 21, an inlet passage 23 which is in fluid communication with the cavity 21 and fluidly connected with the mouthpiece 17 such that an air flow developed by the user on exhaling into the mouthpiece 17 is delivered through the inlet passage 23 into the cavity 21, and an outlet passage 25 which is in fluid communication with the cavity 21 and fluidly connected with the nosepiece 19 such that an air flow delivered into the cavity 21 is delivered through the nosepiece 19.

In this embodiment the inlet passage 23 has a narrow, substantially rectangular section, the downstream end of which opens into the cavity 21 in the housing 15.

The housing 15 further includes an aperture 27, in this embodiment in a lower end thereof, in which a loading member 69 for priming the delivery device is disposed, as will be described in more detail hereinbelow.

The housing 15 further includes a latch element 29, in this embodiment a detent, for latching the loading member 69 when in the primed position, again as will be described in more detail hereinbelow.

The housing 15 further includes at least one, in this embodiment a plurality of external venting apertures 30 which provide for a vent from the cavity 21 in the housing 15 to atmosphere. The venting apertures 30 are normally isolated from the atmosphere by a pressure-sensitive release valve 97, as will be described in more detail hereinbelow, and are opened by opening the pressure-sensitive release valve 97 when a sufficient flow rate cannot be developed through the nosepiece 19, for example, as a result of the nasal passage of the user being congested, and the pressure in the cavity 21 in the housing 15 exceeds a predetermined threshold pressure.

In this embodiment the mouthpiece 17 is configured to be gripped in the lips of the user. In an alternative embodiment the mouthpiece 17 could be configured to be gripped by the teeth of the user and sealed by the lips of the user. In a preferred embodiment the mouthpiece 17 is specifically configured to have one or both of a shape and geometry which allows the delivery device to be gripped repeatedly in the same position, thereby providing for the nosepiece 19 to be reliably inserted in the same position in a nasal cavity.

The nosepiece 19 includes a support member 32 which supports the outlet member 39 of a delivery unit 37, as will be described in more detail hereinbelow. The support member 32, in this embodiment an annular member, includes a central, inner aperture 33 in which the nozzle block 41 of the outlet member 39 of the delivery unit 37 is disposed to deliver substance therefrom, and defines at least one, in this embodiment a plurality of outer apertures 35 about the central aperture 33 through which an air flow developed by an exhalation breath of the user is delivered. In this embodiment the outer apertures 35 are configured, here shaped and dimensioned, such as to direct air flows at the delivered substance as delivered from the nozzle outlet 43 of the nozzle block 41 of the outlet member 39, which air flows interact with the delivered substance such as to optimise the delivery characteristics of the delivered substance.

The delivery device further comprises a delivery unit 37, in this embodiment a pump unit, which is actuatable to deliver a metered dose of substance.

The delivery unit 37 comprises an outlet member 39 which is supported, in this embodiment in a fixed position, by the supporting member 32 of the nosepiece 19, and a container member 40 which contains substance to be delivered and is slideably disposed to the outlet member 39 to deliver a metered volume of substance on driving the container member 40 relative to the outlet member 39.

The outlet member 39 comprises a nozzle block 41 at one, the forward, end thereof which includes a nozzle outlet 43 from which substance is delivered, a piston block 45 at the other, rear end thereof, and a hollow needle 47 which extends from the rear end of the piston block 45 and is fluidly connected to the nozzle outlet 43.

In this embodiment the nozzle outlet 43 is configured to deliver an aerosol of fine liquid droplets of substance on actuation of the delivery unit 37. In an alternative embodiment the nozzle outlet 43 could be configured to provide for the delivery of a liquid jet of substance.

The container member 40 comprises a body 49 which includes a cylinder bore 51, in this embodiment having a cylindrical inner peripheral surface, one, the rear, end of which is closed and the other, forward end of which is open and receives the piston block 45 of the outlet member 39, and a seal element 55 which is disposed in sealing engagement with the cylinder bore 51 such as to define an enclosed chamber 57 containing substance within the cylinder bore 51. The seal element 55 is configured to be rupturable by the hollow needle 47 of the outlet member 39, such that, on driving the container member 40 relative to the outlet member 39, the seal element 55 is driven onto the hollow needle 47 such as to be ruptured by the same, with the contained volume of substance in the chamber 57 being substantially incompressible, and, following rupture of the seal element 55 and with continued driving of the container member 40, substance is delivered through the hollow needle 47 and from the nozzle outlet 43 of the nozzle block 41.

The delivery device further comprises a loading unit 61 which is configured, when actuated, to apply a delivery force to the delivery unit 37, which delivery force is such as to drive the container member 40 of the delivery unit 37 relative to the outlet member 39 of the delivery unit 37, and effect delivery of substance from the nozzle outlet 43 of the nozzle block 41.

The loading unit 61 comprises a drive member 63 which is operative to transmit the delivery force to the delivery unit 37, a restraining member 65 which acts normally to restrain the drive member 63 when loaded by the delivery force and is operable to release the drive member 63, a biasing element 67, in this embodiment a resilient element, here a compression spring, which, when loaded, applies the delivery force to the drive member 63, and a loading member 69 which is operative to load the biasing element 67 to provide the delivery force. In this embodiment the drive member 63 and the restraining member 65 are formed as a single integral unit.

In this embodiment the drive member 63 comprises a cradle 71 in which the container member 40 of the delivery unit 37 is disposed and an outwardly-directed flange 73 which is engaged by the biasing element 67.

In this embodiment the restraining member 65 comprises a tether 75, one end of which is attached to the cradle 71 of the drive member 63 and the other end of which is attached to the housing 15, such that, on loading the cradle 71 with the delivery force, the tether 75 is tensioned. In this embodiment the tether 75 comprises a single filament which is configured to be cut by a cutter element 93 of an actuating member 89, as will be described in more detail hereinbelow, with the cutting of the tether 75 acting to release the restraining member 65. In another embodiment the tether 75 could comprise a plurality of filaments. In preferred embodiments the or each filament could comprise a strand or a sheet.

In this embodiment the restraining member 65 is formed of a plastics material, here Nylon, and the tether 75 is notch sensitized by axial stretching.

In this embodiment the biasing element 67, as compression spring, is disposed about the tether 75 when in the unloaded state such as to protect the tether 75, and thereby prevent release of the restraining member 65 when in the unloaded state.

In this embodiment the loading member 69 comprises a loading button 79 at one, the lower, end thereof, which is typically loaded by the thumb of the user in loading the biasing element 67, an engagement element 81 at the other, upper end thereof which engages the biasing element 67 to load the same, and a support element 83 which interconnects the loading button 79 and the engagement element 81.

In this embodiment the loading button 79 of the loading member 69 includes a peripheral seal 85 which is configured to seal with the aperture 27 in the housing 15 when in the loaded position, as illustrated in FIG. 3(*b*), such as to prevent the escape therefrom of an air flow as delivered into the cavity 21 in the housing 15.

In this embodiment the engagement element 81 of the loading member 69 includes an outwardly-directed flange 87 which acts to prevent the escape of the loading member 69 from the aperture 27 in the housing 15 when in the unloaded position, as illustrated in FIG. 3(*a*), and engages the latching element 29 on the housing 15 to latch the loading member 69 in the loaded position, as illustrated in FIG. 3(*b*).

The delivery device further comprises a breath-actuated actuating member 89 which is disposed in the inlet passage 23 of the housing 15 and operative, on generation of a predetermined force by the exhalation breath of the user, to release the restraining member 65, and thereby effect actuation of the delivery unit 37.

In this embodiment the actuating member 89 comprises a flexible, bi-stable element 91 which is switched from a first, non-actuated state, as illustrated in FIG. 3(*a*), to a second, actuated state, as illustrated in FIG. 3(*d*), on generation of a predetermined actuating force thereat, in this embodiment through the development of a predetermined exhalation flow rate through the mouthpiece 17, and a cutter element 93 which is fixed to the bi-stable element 91, with the cutter element 93 acting to cut the tether 75 of the restraining member 65.

In this embodiment the bi-stable element 91 comprises an elongate band, in a preferred embodiment of a plastics material, here a thermoplastic elastomer (TPE).

In this embodiment the bi-stable element 91 is configured, here one or both of shaped and dimensioned relative to the inlet passage 23 in the housing 15, such as, when in the non-actuated state, to allow an air flow at a first predetermined flow rate through the inlet passage 23 on exhalation by the user through the mouthpiece 17, and, when switched to the actuated state, to be moved clear of the inlet passage 23 and provide for the delivery of an air flow at a second, higher flow rate through the inlet passage 23, and hence the nosepiece 19, which interacts with the delivered substance.

In alternative embodiments the bi-stable element 91 can be configured such as to provide alternative flow schemes, for example, in closing the inlet passage 23 in both the non-actuated and actuated states, in closing the inlet passage 23 when in the non-actuated state and providing for an air flow through the inlet passage 23 when in the actuated state, in providing for an air flow through the inlet passage 23 when in the non-actuated state and closing the inlet passage 23 when in the actuated state, and in providing for a uniform flow rate through the inlet passage 23 when in the actuated and non-actuated states.

In this embodiment the delivery device further comprises a pressure-sensitive release valve 97 which acts to provide for a flow through the inlet passage 23 in the housing 15 when the pressure in the cavity 21 in the housing 15 exceeds a predetermined pressure, as caused by at least partial obstruction of the nasal airway of the user.

In this embodiment the pressure-sensitive release valve 97 comprises a resilient flap element 99 which normally doses the venting apertures 30 in the housing 15, but is displaced from the venting apertures 30 on the generation of a predetermined pressure in the cavity 21 in the housing 15, such as to allow an air flow therethrough.

Operation of the delivery device will now be described hereinbelow with reference to FIGS. 3(a) to (g).

Figure 3A:
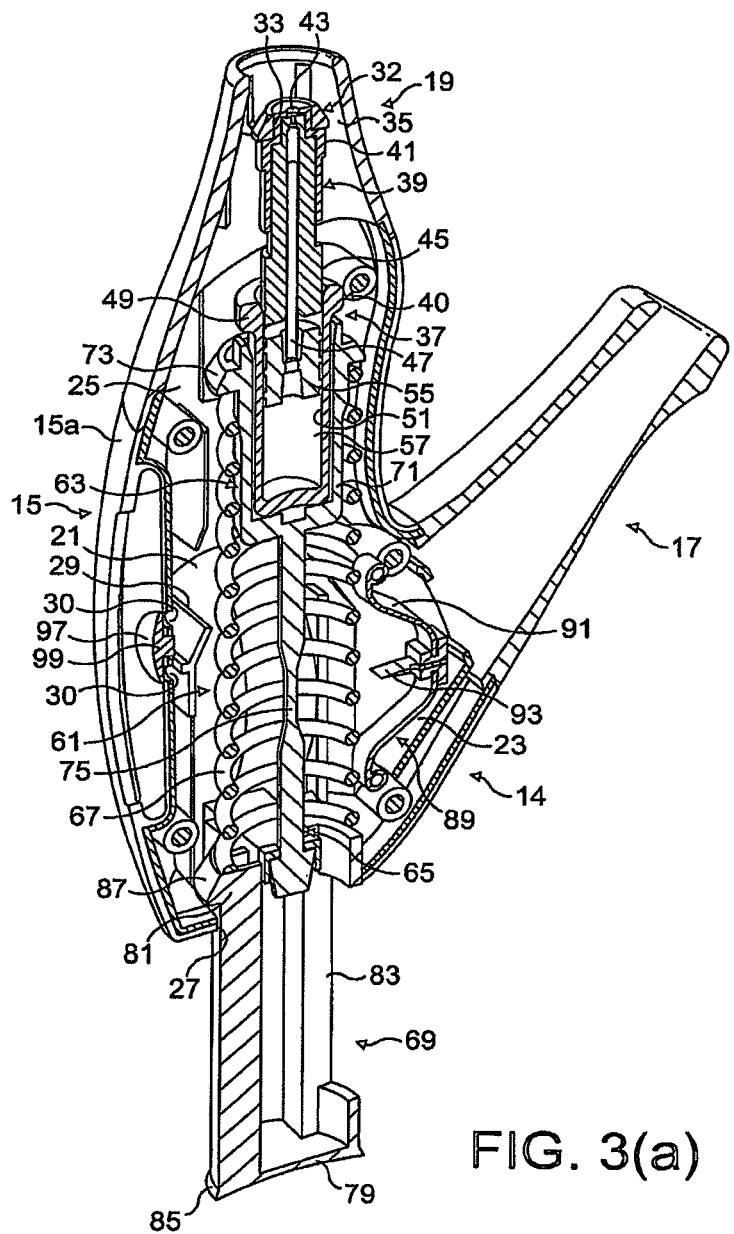
FIG. 3(a) illustrates a vertical sectional view of the delivery device of FIG. 1, where in a first, rest or inoperative configuration.
Figure 3B:
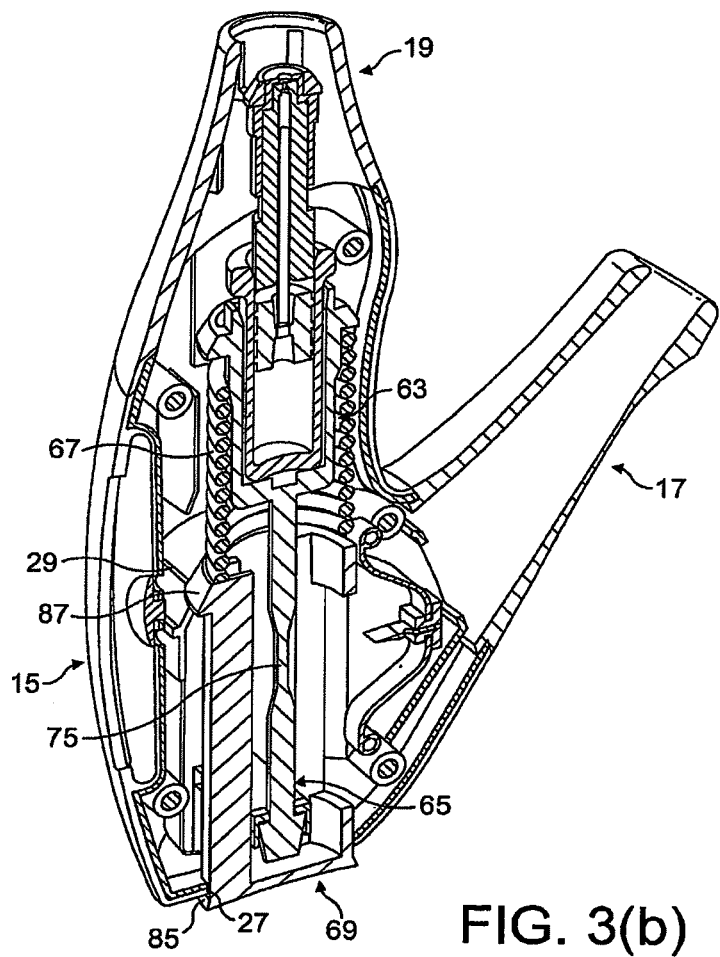
FIG. 3(b) illustrates a vertical sectional view of the delivery device of FIG. 1, where in a loaded configuration.

The user first takes the delivery device, as illustrated in FIG. 3(a), and primes the delivery device by depressing the loading member 69 until latched in the primed position in the housing 15, as illustrated in FIG. 3(b). In this embodiment, as described hereinabove, the loading member 69 is latched in the primed position by engagement of the flange 87 thereof with the latch element 29 of the housing 15, in which position the peripheral seal 85 of the loading member 69 is in sealing engagement with the aperture 27 in the lower end of the housing 15.

In this configuration, the biasing element 67 is biased, here through compression of the compression spring, such as to load the drive member 63 with a predetermined delivery force, with the tether 75 of the restraining mechanism 65 being tensioned by the delivery force.

Figure 3C:
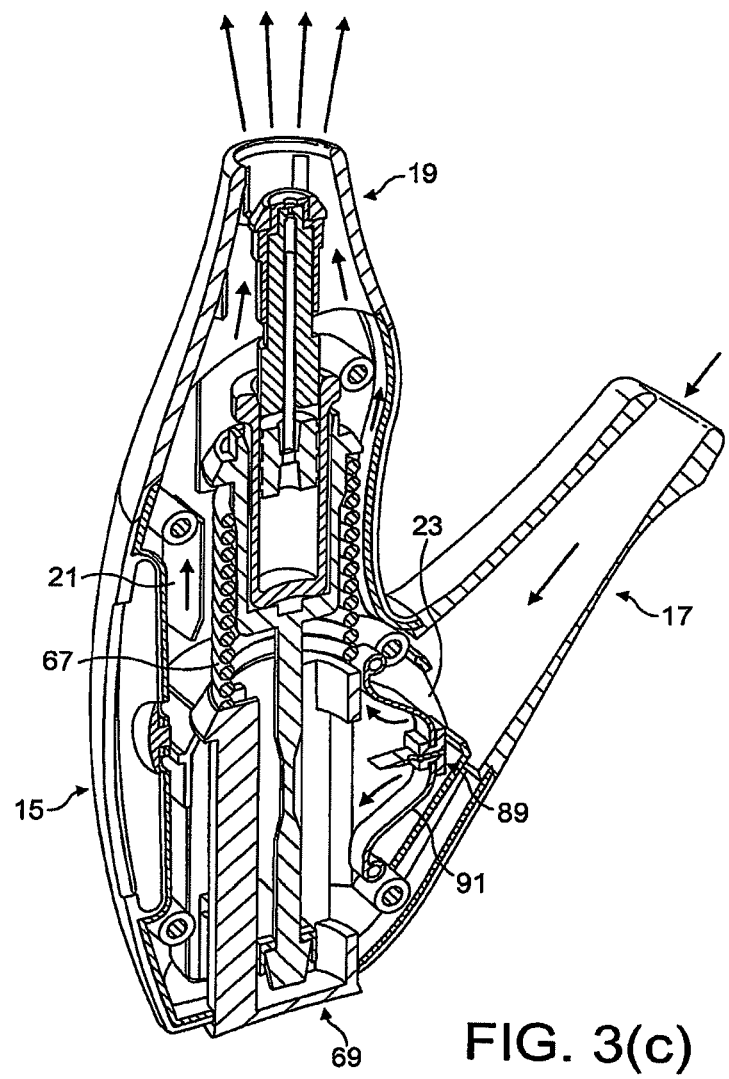
FIG. 3(c) illustrates a vertical sectional view of the delivery device of FIG. 1, with the subject commencing exhalation through the mouthpiece.

The user then inserts the nosepiece 19 in one of his/her nostrils, grips the mouthpiece 17 in his/her lips, and commences exhaling through the mouthpiece 17, as illustrated in FIG. 3(c). The air flow developed by exhalation through the mouthpiece 17 passes through the cavity 21 in the housing 15 and into the nasal airway of the user through the nosepiece 19.

In this embodiment the delivery device is configured normally to deliver the exhalation breath through one nostril of the user such as to flow around the posterior margin of the nasal septum and out of the other nostril of the user, thereby achieving a bi-directional flow through the nasal cavities as disclosed in WO-A-00/51672.

Figure 3D:
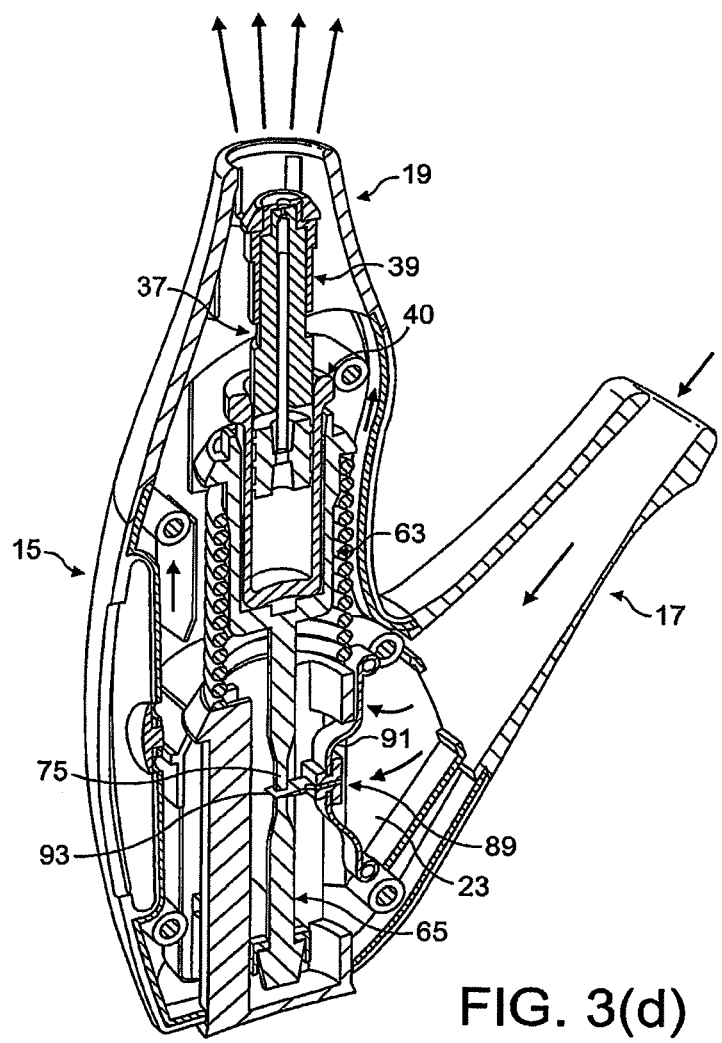
FIG. 3(d) illustrates a vertical sectional view of the delivery device of FIG. 1, where the actuating member of the breath-actuation mechanism is operated by the exhalation of the subject developing an actuation force.

In exhaling through the mouthpiece 17, the developed air flow is restricted by the presence of the bi-stable element 91 of the actuating member 89 in the inlet passage 23 of the housing 15, such that an actuation force is applied to the bi-stable element 91. On reaching a predetermined flow rate, the actuation force is such as to switch the bi-stable element 91 from the non-actuated state, as illustrated in FIG. 3(c), to the actuated state, as illustrated in FIG. 3(d).

In being switched to the actuated state, the bi-stable element 91 acts to drive the cutter element 93, which is fixed thereto, to cut the tether 75 of the restraining member 65, which acts to release the drive member 63 to actuate the delivery unit 37 by driving the container member 40 of the delivery unit 37 relative to the outlet member 39 of the delivery unit 37, and the bi-stable element 91 is also moved clear of the inlet passage 23 of the housing 15, such as to provide for the generation of a higher flow rate through the inlet passage 23, and hence the nosepiece 19, which interacts with substance which is to be delivered.

Figure 3E:
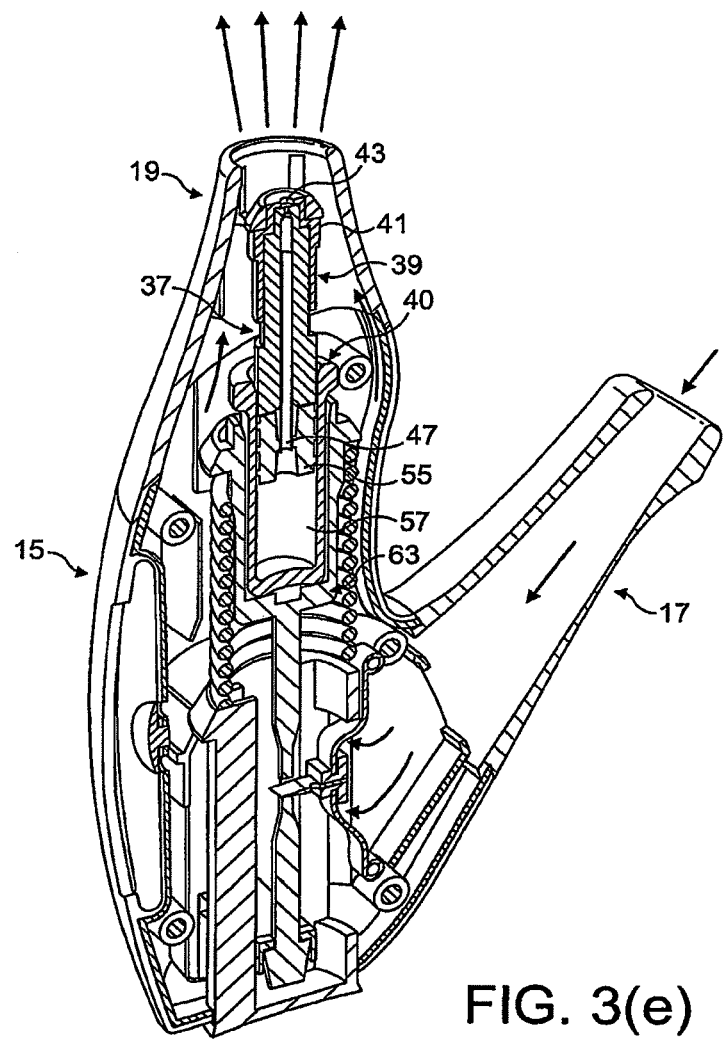
FIG. 3(e) illustrates a vertical sectional view of the delivery device of FIG. 1, where the delivery unit is actuated to open the substance reservoir thereof.

Following release of the drive member 63, in a first phase as illustrated in FIG. 3(e), the drive member 63 acts to drive the container member 40 relative to the outlet member 39 such as to cause the hollow needle 47 of the outlet member 39 to rupture the seal element 55 and provide for fluid communication between the chamber 57 of the container member 40 which contains the substance to be delivered and the nozzle outlet 43 of the nozzle block 41 of the outlet member 39.

Figure 3F:
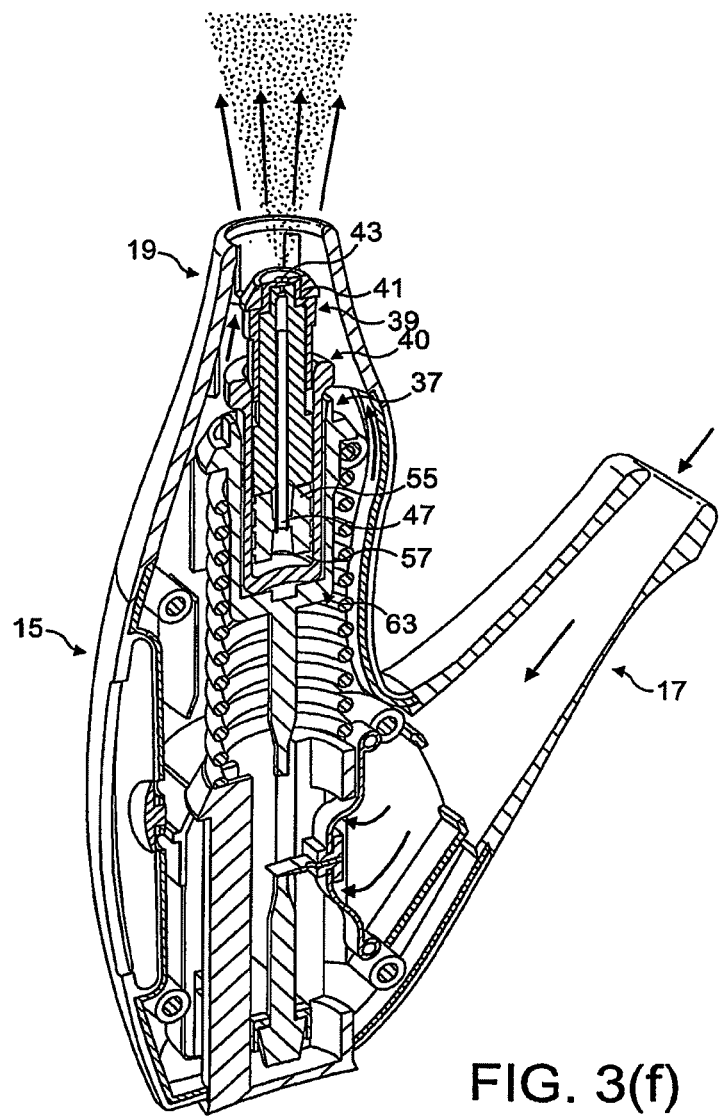
FIG. 3(f) illustrates a vertical sectional view of the delivery device of FIG. 1, where the delivery unit is actuated to deliver substance from the nosepiece.

Following the rupturing of the seal element 55, in a second phase as illustrated in FIG. 3(f), the drive member 63 acts further to drive the container member 40 relative to the outlet member 39 such as to expel the metered volume of substance from the chamber 57 of the container member 40 and from the nozzle outlet 43 of the nozzle block 41 of the outlet member 39, in this embodiment as an aerosol of liquid droplets of substance.

Figure 3G:
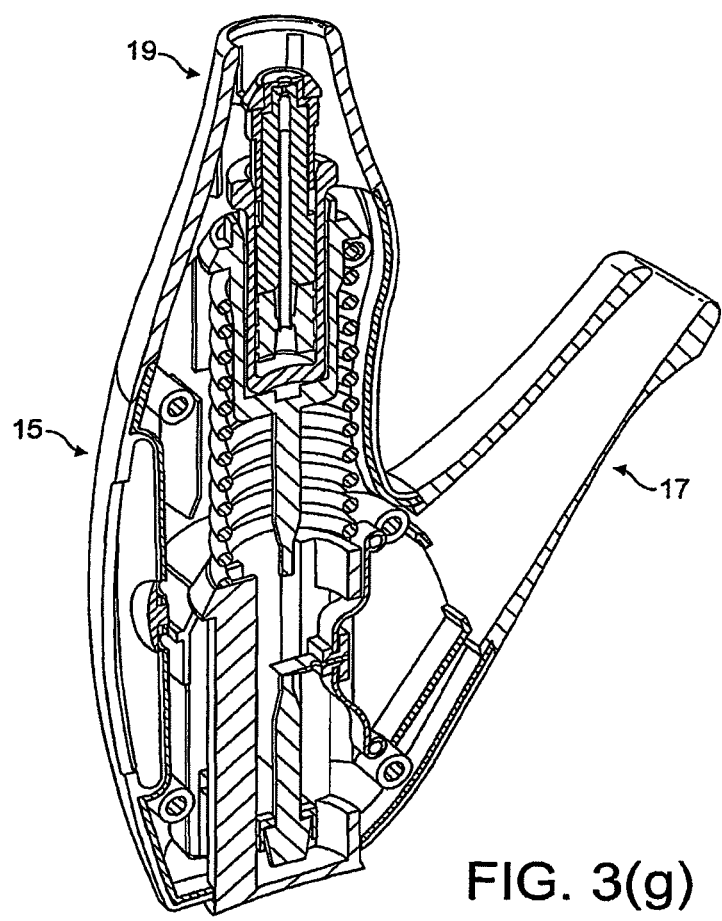
FIG. 3(g) illustrates a vertical sectional view of the delivery device of FIG. 1, following operation of the delivery device.

Following actuation of the delivery device, as illustrated in FIG. 3(g), the user then ceases exhaling and removes the device from his her/her mouth and nostril.

Figure 4:
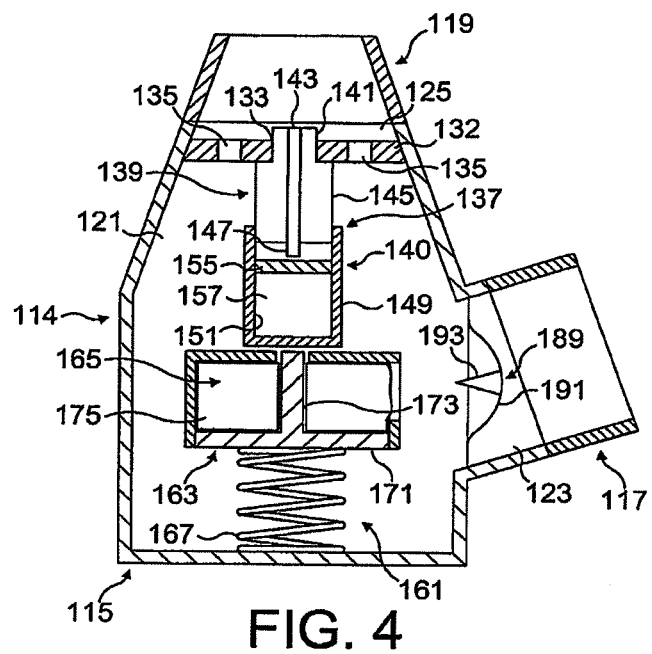
FIG. 4 illustrates a nasal delivery device in accordance with a second embodiment of the present invention.
Figure 5A:
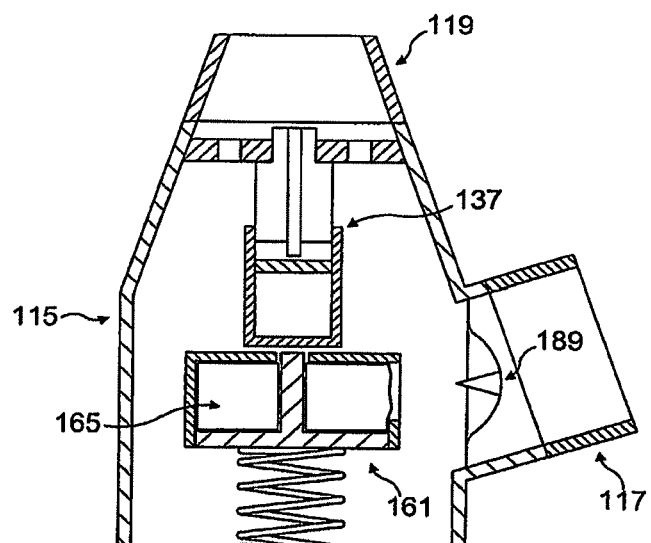
FIG. 5(a) illustrates the delivery device of FIG. 4, where in a first, rest or inoperative configuration.
Figure 5B:
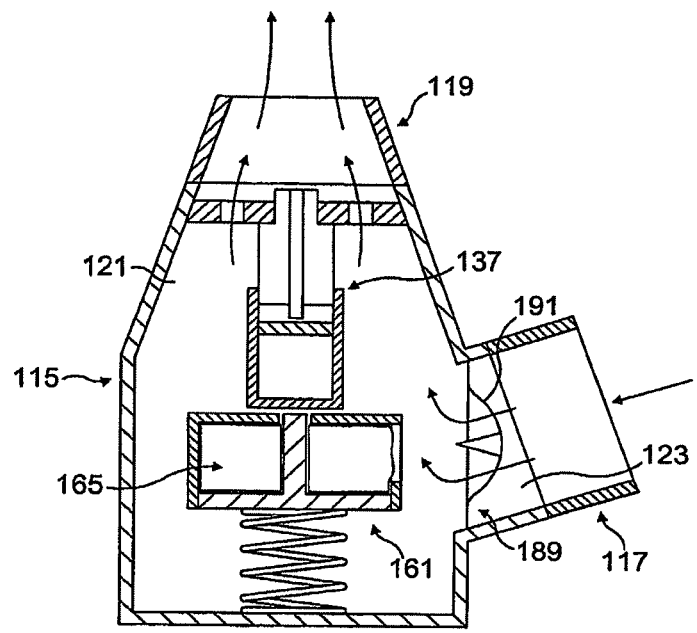
FIG. 5(b) illustrates the delivery device of FIG. 4, with the subject commencing exhalation through the mouthpiece.
Figure 5C:
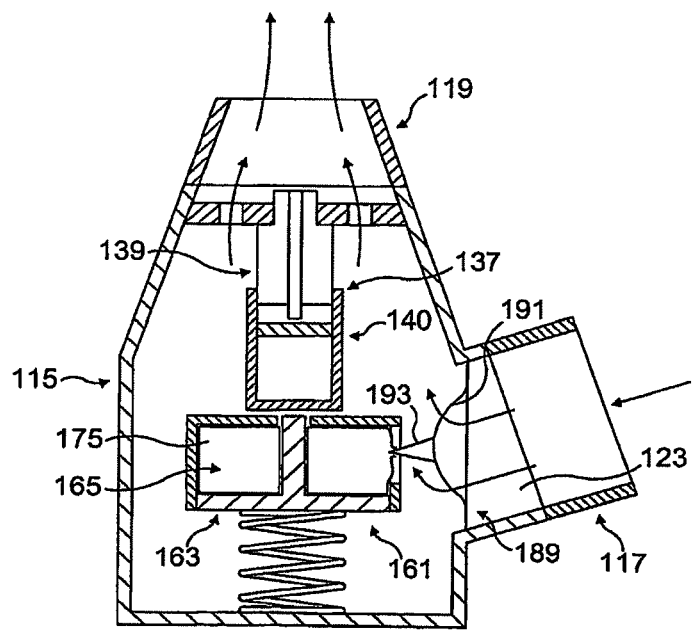
FIG. 5(c) illustrates the delivery device of FIG. 4, where the actuating member of the breath-actuation mechanism is operated by the exhalation of the subject developing an actuation force.
Figure 5D:
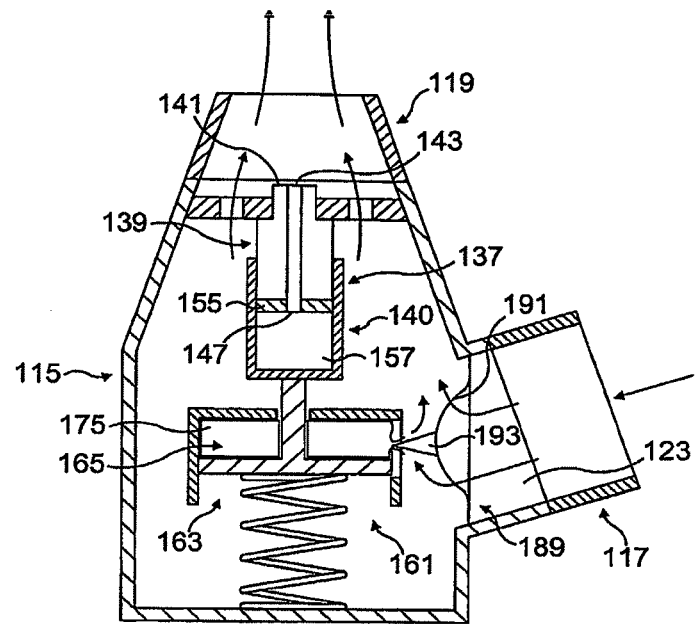
FIG. 5(d) illustrates the delivery device of FIG. 4, where the delivery unit is actuated to open the substance reservoir thereof.
Figure 5E:
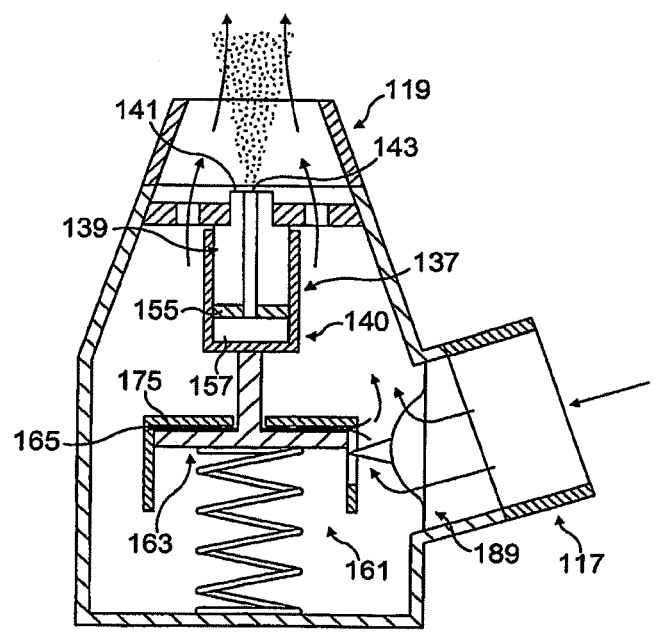
FIG. 5(e) illustrates the delivery device of FIG. 4, where the delivery unit is actuated to deliver substance from the nosepiece.
Figure 5F:
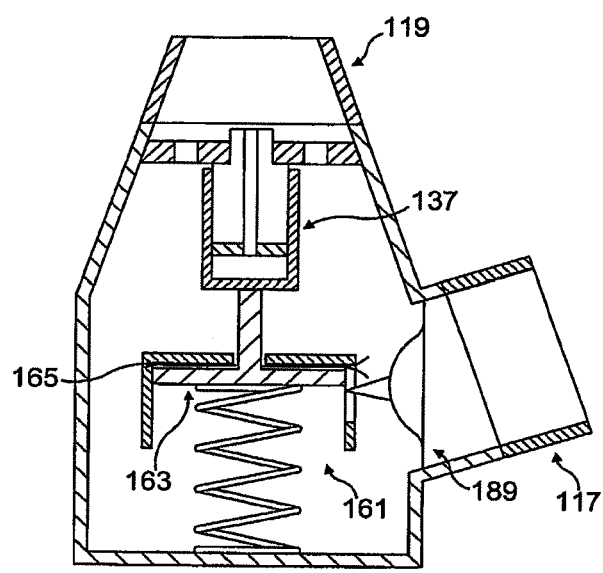
FIG. 5(f) illustrates the delivery device of FIG. 4, following operation of the delivery device.

FIGS. 4 and 5 illustrate a breath-actuated nasal delivery device in accordance with a second embodiment of the present invention.

The delivery device comprises a body unit 114 which comprises a housing 115, which is typically gripped in the hand of a user, a mouthpiece 117 through which the user exhales to actuate the delivery device, and a nosepiece 119 for fitting to a nostril of the user and through which substance is delivered to the nasal airway of the user.

The housing 115 includes a cavity 121, an inlet passage 123 which is in fluid communication with the cavity 121 and fluidly connected with the mouthpiece 117 such that an air flow developed by the user on exhaling into the mouthpiece 117 is delivered through the inlet passage 123 into the cavity 121, and an outlet passage 125 which is in fluid communication with the cavity 121 and fluidly connected with the nosepiece 119 such that an air flow delivered into the cavity 121 is delivered through the nosepiece 119.

In this embodiment the inlet passage 123 has a narrow, substantially rectangular section, the downstream end of which opens into the cavity 121 in the housing 115.

In this embodiment the mouthpiece 117 is configured to be gripped in the lips of the user. In an alternative embodiment the mouthpiece 117 could be configured to be gripped by the teeth of the user and sealed by the lips of the user. In a preferred embodiment the mouthpiece 117 is specifically configured to have one or both of a shape and geometry which allows the delivery device to be gripped repeatedly in the same position, thereby providing for the nosepiece 119 to be reliably inserted in the same position in a nasal cavity.

The housing 115 includes a support member 132 which supports the outlet member 139 of a delivery unit 137, as will be described in more detail hereinbelow. The support member 132, in this embodiment an annular member, includes a central, inner aperture 133 in which the nozzle block 141 of the outlet member 139 of the delivery unit 137 is disposed to deliver substance therefrom, and at least one, in this embodiment a plurality of outer apertures 135 about the central aperture 133 through which an air flow developed through the cavity 121 in the housing 115 is delivered. In this embodiment the outer apertures 135 are configured, here shaped and dimensioned, such as to direct air flows at the delivered substance as delivered from the nozzle outlet 143 of the nozzle block 141 of the outlet member 139, which air flows interact with the delivered substance such as to optimise the delivery characteristics of the delivered substance.

The delivery device further comprises a delivery unit 137, in this embodiment a pump unit, which is actuatable to deliver a metered dose of substance.

The delivery unit 137 comprises an outlet member 139 which is supported, in this embodiment in a fixed position, by the supporting member 132 of the housing 115, and a container member 140 which contains substance to be delivered and is slideably disposed to the outlet member 139 to deliver a metered volume of substance on driving the container member 140 relative to the outlet member 139.

The outlet member 139 comprises a nozzle block 141 at one, the forward, end thereof which includes a nozzle outlet 143 from which substance is delivered, a piston block 145 at the other, rear end thereof, and a hollow needle 147 which extends from the rear end of the piston block 145 and is fluidly connected to the nozzle outlet 143.

In this embodiment the nozzle outlet 143 is configured to deliver an aerosol of fine liquid droplets of substance on actuation of the delivery unit 137. In an alternative embodiment the nozzle outlet 143 could be configured to provide for the delivery of a liquid jet of substance.

The container member 140 comprises a body 149 which includes a cylinder bore 151, in this embodiment having a cylindrical inner peripheral surface, one, the rear, end of which is closed and the other, forward end of which is open and receives the piston block 145 of the outlet member 139, and a seal element 155 which is disposed in sealing engagement with the cylinder bore 151 such as to define an enclosed chamber 157 containing substance within the cylinder bore 151. The seal element 155 is configured to be rupturable by the hollow needle 147 of the outlet member 139, such that, on driving the container member 140 relative to the outlet member 139, the seal element 155 is driven onto the hollow needle 147 such as to be ruptured by the same, with the contained volume of substance in the chamber 157 being substantially incompressible, and, following rupture of the seal element 155 and with continued driving of the container member 140, substance is delivered through the hollow needle 147 and from the nozzle outlet 143 of the nozzle block 141.

The delivery device further comprises a loading unit 161 which is configured, when actuated, to apply a delivery force to the delivery unit 137, which delivery force is such as to drive the container member 140 of the delivery unit 137 relative to the outlet member 139 of the delivery unit 137, and effect delivery of substance from the nozzle outlet 143 of the nozzle block 141.

The loading unit 161 comprises a drive member 163 which is operative to transmit the delivery force to the delivery unit 137, a restraining member 165 which acts normally to restrain the drive member 163 when loaded by the delivery force and is operable to release the drive member 163, and a biasing element 167, in this embodiment a resilient element, here a compression spring, which applies the delivery force to the drive member 163.

In this embodiment the drive member 163 comprises a support element 171 which is loaded on one, the rear, side thereof by the loading force of the biasing element 167 and supported on the other, forward side thereof by the restraining member 165, and a drive element 173, in this embodiment a projecting lug, which extends from the forward side of the support element 171 in opposed relation to the container member 140 of the delivery unit 137.

In this embodiment the restraining member 165 comprises a gas support cushion 175 which, when normally inflated, here with air, acts to hold the drive member 163 against the bias of the biasing element 167, and, when punctured, collapses such as to allow the biasing element 167 to drive the drive member 163. In this embodiment the gas support cushion 175 is configured such as to be punctured by a cutter element 193 of an actuating member 189 to actuate the delivery unit 137, as will be described in more detail hereinbelow, with the puncturing of the gas support cushion 175 acting advantageously to provide a supplementary air flow.

The delivery device further comprises a breath-actuated actuating member 189 which is disposed in the inlet passage 123 of the housing 115 and operative, on generation of a predetermined force by the exhalation breath of the user, to release the restraining member 165, and thereby effect actuation of the delivery unit 137.

In this embodiment the actuating member 189 comprises a flexible, bi-stable element 191 which is switched from a first, non-actuated state, as illustrated in FIGS. 5(*a*) and (*b*), to a second, actuated state, as illustrated in FIG. 5(*c*), on generation of a predetermined actuating force thereat, in this embodiment through the development of a predetermined exhalation flow rate through the mouthpiece 117, and a cutter element 193 which is fixed to the bi-stable element 191, with the cutter element 193 acting to puncture the gas support cushion 175 of the restraining member 165.

In this embodiment the bi-stable element 191 comprises an elongate band, in a preferred embodiment of a plastics material, here a thermoplastic elastomer (TPE).

In this embodiment the bi-stable element 191 is configured, here one or both of shaped and dimensioned relative to the inlet passage 123 in the housing 115, such as, when in the non-actuated state, to allow an air flow at a first predetermined flow rate through the inlet passage 123 on exhalation by the user through the mouthpiece 117, and, when switched to the actuated state, to be moved clear of the inlet passage 123 and provide for the delivery of an air flow at a second, higher flow rate through the inlet passage 123, and hence the nosepiece 119, which interacts with the delivered substance.

In alternative embodiments the bi-stable element 191 can be configured such as to provide alternative flow schemes, for example, in closing the inlet passage 123 in both the non-actuated and actuated states, in closing the inlet passage 123 when in the non-actuated state and providing for an air flow through the inlet passage 123 when in the actuated state, in providing for an air flow through the inlet passage 123 when in the non-actuated state and closing the inlet passage 123 when in the actuated state, and in providing for a uniform flow rate through the inlet passage 123 when in the actuated and non-actuated states.

Operation of the delivery device will now be described hereinbelow with reference to FIGS. 5(*a*) to (*f*).

The user first takes the delivery device, as illustrated in FIG. 5(*a*), and inserts the nosepiece 119 in one of his/her nostrils, and grips the mouthpiece 117 in his/her lips.

The user then commences exhaling through the mouthpiece 117, as illustrated in FIG. 5(*b*). The air flow developed by exhalation through the mouthpiece 117 passes through the cavity 121 in the housing 115 and into the nasal airway of the user through the nosepiece 119.

In this embodiment the delivery device is configured normally to deliver the exhalation breath through one nostril of the user such as to flow around the posterior margin of the nasal septum and out of the other nostril of the user, thereby achieving a bi-directional flow through the nasal cavities as disclosed in WO-A-00/51672.

In exhaling through the mouthpiece 117, the developed air flow is restricted by the presence of the bi-stable element 191 of the actuating member 189 in the inlet passage 123 of the housing 115, such that an actuation force is applied to the bi-stable element 191. On reaching a predetermined flow rate, the actuation force is such as to switch the bi-stable element 191 from the non-actuated state, as illustrated in FIG. 5(*b*), to the actuated state, as illustrated in FIG. 5(*c*).

In being switched to the actuated state, the bi-stable element 191 acts to drive the cutter element 193, which is fixed thereto, to puncture the gas support cushion 175 of the restraining member 165, which acts to release the drive member 163 to actuate the delivery unit 137 by driving the container member 140 of the delivery unit 137 relative to the outlet member 139 of the delivery unit 137, and the bi-stable element 191 is also moved clear of the inlet passage 123 of the housing 115, such as to provide for the generation of a higher flow rate through the inlet passage 123, which flow as developed by the exhalation breath together with the flow as developed by the escaping air flow from the gas support cushion 175 is delivered through the nosepiece 119 to interact with substance which is to be delivered from the delivery unit 137.

Following release of the drive member 163, in a first phase as illustrated in FIG. 5(*d*), the drive member 163 acts to drive the container member 140 relative to the outlet member 139 such as to cause the hollow needle 147 of the outlet member 139 to rupture the seal element 155 and provide for fluid communication between the chamber 157 of the container member 140 which contains the substance to be delivered and the nozzle outlet 143 of the nozzle block 141 of the outlet member 139.

Following the rupturing of the seal element 155, in a second phase as illustrated in FIG. 5(*e*), the drive member 163 acts further to drive the container member 140 relative to the outlet member 139 such as to expel the metered volume of substance from the chamber 157 of the container member 140 and from the nozzle outlet 143 of the nozzle block 141 of the outlet member 139, in this embodiment as an aerosol of liquid droplets of substance.

Following actuation of the delivery device, as illustrated in FIG. 5(*f*), the user then ceases exhaling and removes the device from his her/her mouth and nostril.

Figure 6:
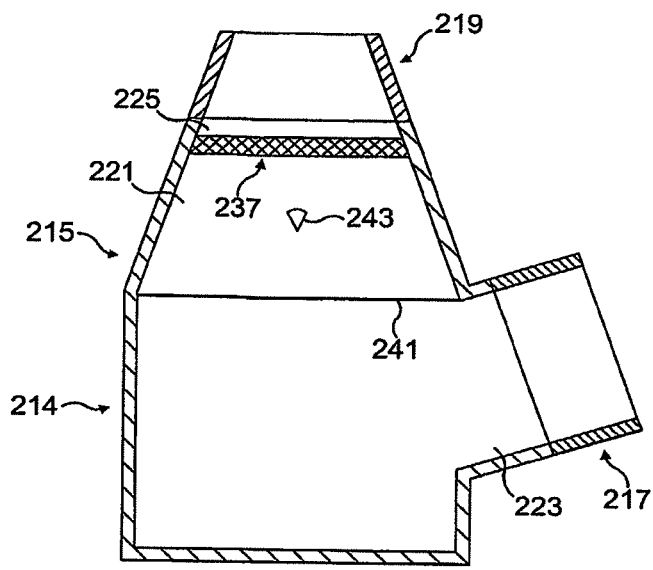
FIG. 6 illustrates a nasal delivery device in accordance with a third embodiment of the present invention.
Figure 7A:
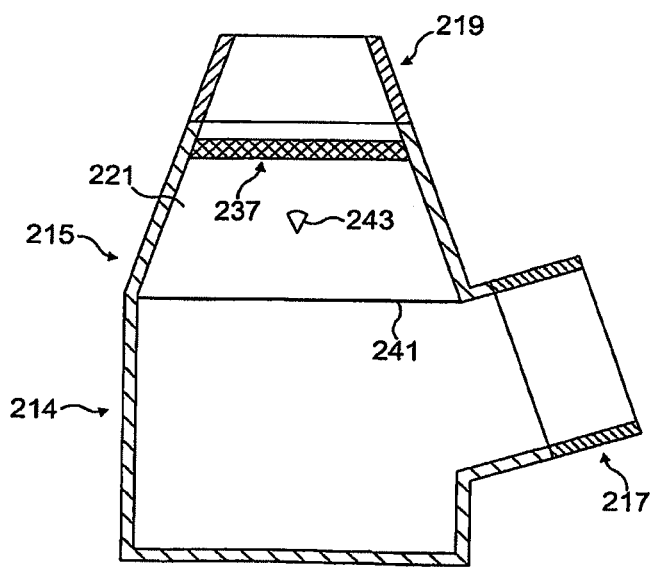
FIG. 7(a) illustrates the delivery device of FIG. 6, where in a first, rest or inoperative configuration.
Figure 7B:
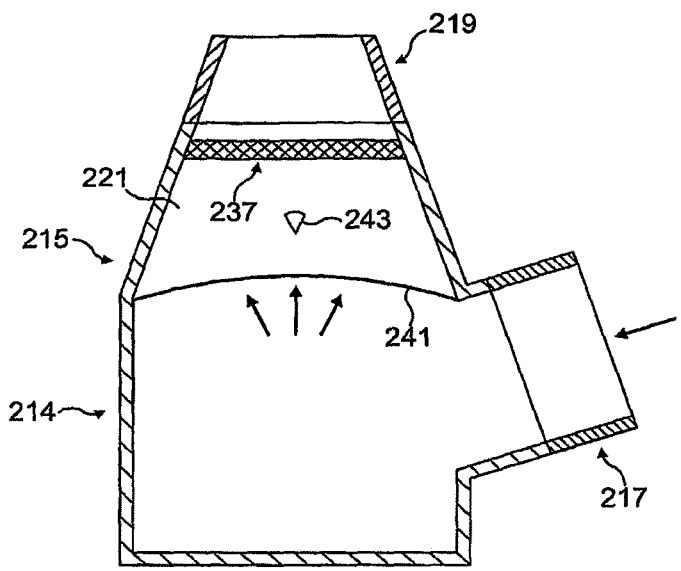
FIG. 7(b) illustrates the delivery device of FIG. 6, with the subject commencing exhalation through the mouthpiece.
Figure 7C:
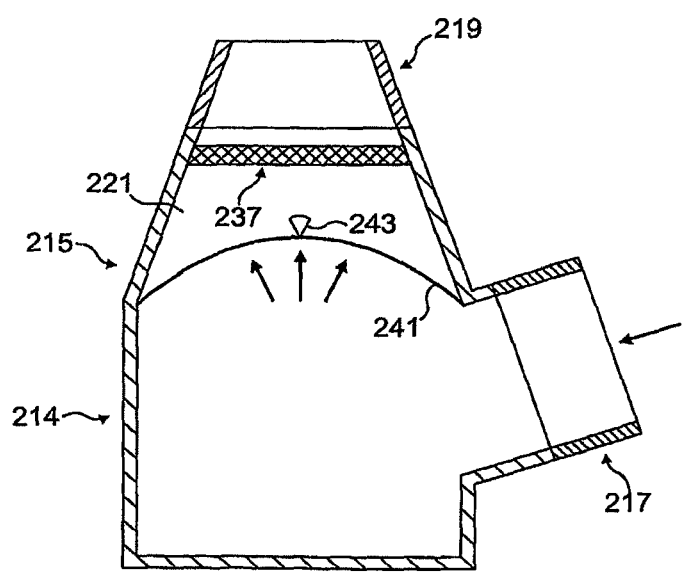
FIG. 7(c) illustrates the delivery device of FIG. 6, where the subject has continued exhaling and the flexible diaphragm is deflected to a predetermined extent which corresponds to the exhaled air contained thereby having a predetermined pressure.
Figure 7D:
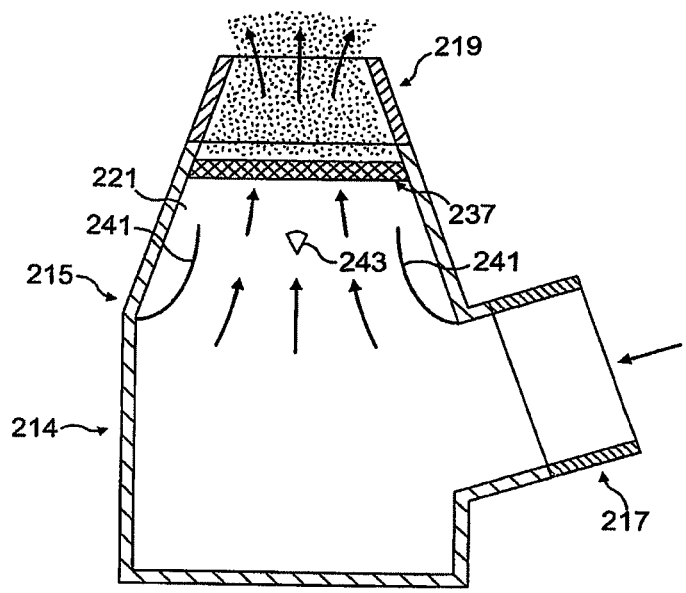
FIG. 7(d) illustrates the delivery device of FIG. 6, where the flexible diaphragm has been ruptured to release the pressurized air as contained thereby.
Figure 7E:
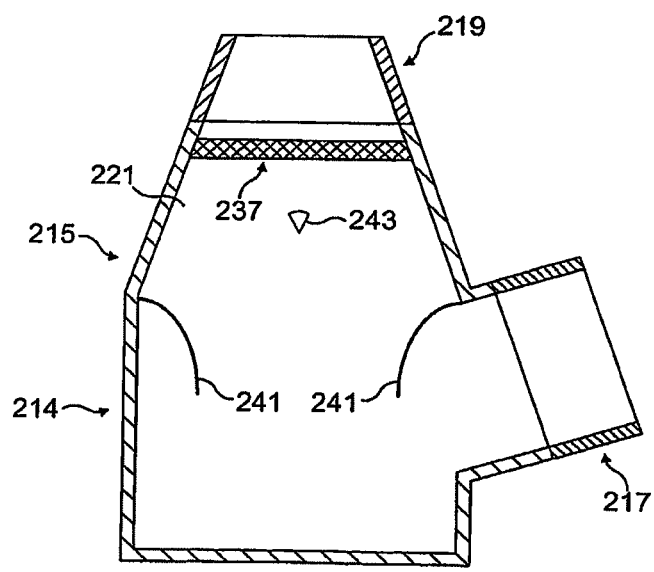
FIG. 7(e) illustrates the delivery device of FIG. 6, following operation of the delivery device.
Figure 8:
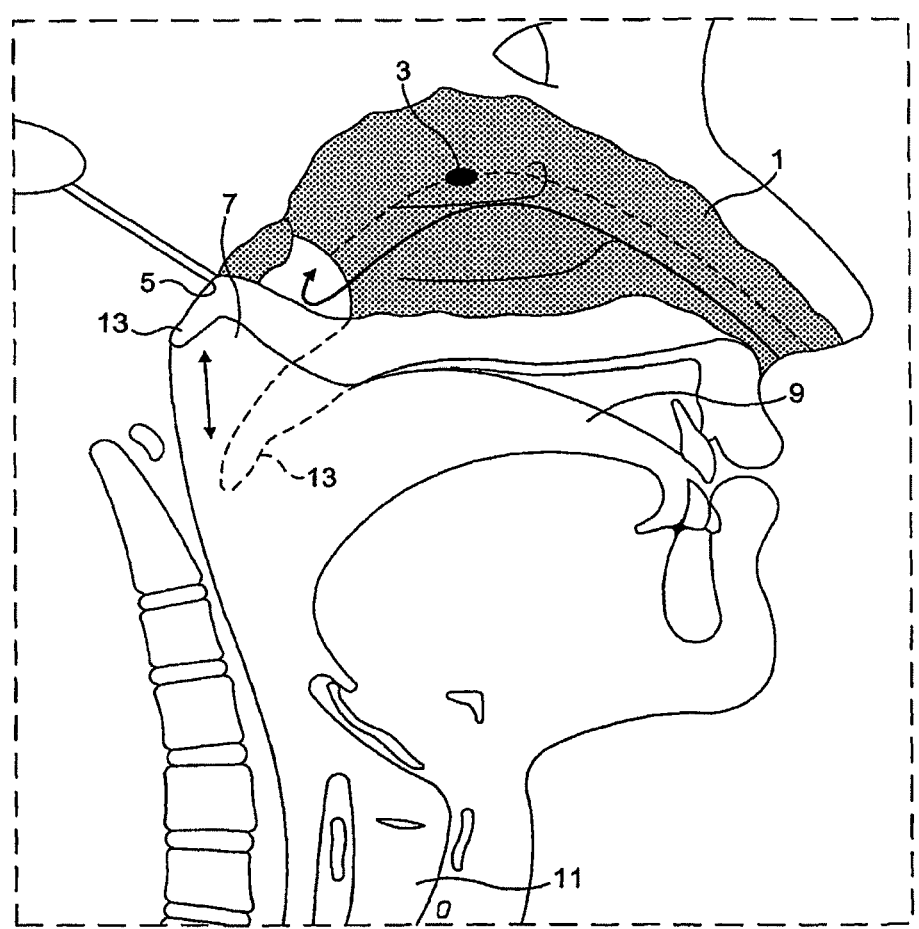
FIG. 8 schematically illustrates the anatomy of the upper respiratory tract of a human subject.

FIGS. 6 and 7 illustrate a breath-actuated nasal delivery device in accordance with a third embodiment of the present invention.

The delivery device comprises a body unit 214 which comprises a housing 215, which is typically gripped in the hand of a user, a mouthpiece 217 through which the user exhales to actuate the delivery device, and a nosepiece 219 for fitting to a nostril of the user and through which substance is delivered to the nasal airway of the user.

The housing 215 includes a cavity 221, an inlet passage 223 which is in fluid communication with the cavity 221 and fluidly connected with the mouthpiece 217 such that an air flow developed by the user on exhaling into the mouthpiece 217 is delivered through the inlet passage 223 into the cavity 221, and an outlet passage 225 which is in fluid communication with the cavity 221 and fluidly connected with the nosepiece 219 such that an air flow delivered from the cavity 221 is delivered through the nosepiece 219.

In this embodiment the mouthpiece 217 is configured to be gripped in the lips of the user. In an alternative embodiment the mouthpiece 217 could be configured to be gripped by the teeth of the user and sealed by the lips of the user. In a preferred embodiment the mouthpiece 217 is specifically configured to have one or both of a shape and geometry which allows the delivery device to be gripped repeatedly in the same position, thereby providing for the nosepiece 219 to be reliably inserted in the same position in a nasal cavity.

The delivery device further comprises a delivery unit 237 which provides for the delivery of a metered dose of substance.

In this embodiment the delivery unit 237 comprises an impregnated structure, typically a porous mat, as impregnated with a metered dose of substance, either as a liquid or a powder, with the substance being entrained in an air flow as delivered thereover.

In alternative embodiments the delivery unit 237 could be of any of the kinds as described hereinabove in relation to the other-described embodiments which provide for the delivery of substance.

The delivery device further comprises a flexible diaphragm 241, in this embodiment a resilient element, which is disposed in the housing 215 and closes, or at least substantially closes, the flow path from the mouthpiece 217 to the nosepiece 219, and a rupturing element 243 which is operative to rupture the diaphragm 241 where the diaphragm 241 is subjected to a predetermined actuation pressure. With this configuration, exhalation by a user into the mouthpiece 217 acts to bias the diaphragm 241, as illustrated in FIGS. 7(*b*) and (*c*), much in the manner of inflating a balloon, and, when the diaphragm 241 is deflected to a predetermined extent, which corresponds to the generation of a predetermined pressure upstream of the diaphragm 241, the rupturing element 243 acts to rupture the diaphragm 241, causing the contained pressurized air to be driven out of the nosepiece 219, as illustrated in FIG. 7(*d*).

Operation of the delivery device will now be described hereinbelow with reference to FIGS. 7(*a*) to (*e*).

The user first takes the delivery device, as illustrated in FIG. 7(*a*), and inserts the nosepiece 219 in one of his/her nostrils, and grips the mouthpiece 217 in his/her lips.

The user then commences exhaling through the mouthpiece 217, as illustrated in FIG. 7(*b*). The air flow developed by exhalation through the mouthpiece 217 passes into the cavity 221 in the housing 215 and is contained by the diaphragm 241, causing the diaphragm 241 to be deflected.

With continued exhalation, the diaphragm 241 is further deflected until such point as the diaphragm 241 is deflected to a predetermined extent, which corresponds to the generation of a predetermined pressure upstream of the diaphragm 241, as illustrated in FIG. 7(*c*).

At this point, the rupturing element 243 acts to rupture the diaphragm 241, causing the contained pressurized air to be driven out of the nosepiece 219 as a sudden burst of air, as illustrated in FIG. 7(*d*), where this air flow entrains a metered dose of substance as provided by the delivery unit 237.

In this embodiment the pressure of the air flow is such as normally to deliver an air flow through the one nostril, around the posterior margin of the nasal septum and out of the other nostril of the user, thereby achieving a bi-directional flow through the nasal cavities as disclosed in WO-A-00/51672.

Following actuation of the delivery device, as illustrated in FIG. 7(*e*), the user then ceases exhaling and removes the device from his her/her mouth and nostril.

Finally, it will be understood that the present invention has been described in its preferred embodiments and can be modified in many different ways without departing from the scope of the invention as defined by the appended claims.

In one alternative embodiment the delivery unit 37, 137 could comprise an aerosol canister, such as used in a pressurized metered dose inhaler (pMDI), for delivering a propellant, preferably a hydrofluoroalkane (HFA) propellant or the like, containing substance, preferably a medicament either as a suspension or a solution.

In another alternative embodiment the delivery unit 37, 137 could comprise a dry powder delivery unit for delivering a metered dose of substance in a dry powder.

In other embodiments the delivery unit 37, 137 could be configured to re-constitute substance on actuation thereof, typically by admixing at least two liquids to provide a re-constituted liquid substance, at least one liquid and at least one powder to provide a re-constituted liquid substance, and at least two powders to provide a re-constituted powder substance.

In yet another alternative embodiment the cutter element 93 could be omitted from the actuating member 89, and instead be disposed to the housing 15 in opposed relation to actuating member 89 such that the actuating member 89 acts to deflect the tether 75 of the restraining member 65 onto the cutter element 93 so as to cut the tether 75.

In still another alternative embodiment the tether 75 of the restraining member 65 could be configured such as to be broken in some other manner. For example, the tether 75 could be formed of a brittle material which has a high tensile strength but a low bending strength, allowing for fracture of the tether 75 by deflection of the tether 75.

In yet another alternative embodiment the pressure-sensitive release valve 97 could be replaced by a flexible diaphragm, where defining part of the cavity 21 in the housing 15, which is coupled to the actuating member 89. With this configuration, the diaphragm is deflected when the pressure in the cavity 21 in the housing 15 exceeds a predetermined pressure, as caused by at least partial obstruction of the nasal airway of the user, with the deflection of the diaphragm causing actuation of the coupled actuating member 89.

In still another alternative embodiment the bi-stable element 91, 191 of the actuating member 89, 189 could close the inlet passage 23, 123 of the housing 15, 115 such as to provide for actuation of the actuating member 89, 189 on generation of a predetermined actuation pressure in the mouthpiece 17, 117.

In the described embodiments the bi-stable element 91, 191 of the actuating member 89, 189 has equal bi-stable states, but in alternative embodiments the bi-stable element 91, 191 of the actuating member 89, 189 has unequal bi-stable states, whereby the actuating force required to switch the bi-stable element 91, 191 to the actuated state is less than the force as would be required to switch the bi-stable element 91, 191 from the actuated state to the non-actuated state.

What is claimed is:

1. A delivery device comprising:
   a mouthpiece adapted for a subject to exhale through;
   an air channel which is in fluid communication with the mouthpiece;
   a flexible diaphragm which is disposed in the air channel, the diaphragm restricting air flow through the air channel until pressure in the mouthpiece equals or exceeds a predetermined actuation pressure; and
   a rupturing element for rupturing the diaphragm when the pressure in the mouthpiece equals or exceeds the predetermined actuation pressure.

2. The delivery device of claim 1, wherein the diaphragm at least partially closes the air channel until the predetermined actuation pressure is developed in the mouthpiece.

3. The delivery device of claim 2, wherein the diaphragm closes the air channel until the predetermined actuation pressure is developed in the mouthpiece.

4. The delivery device of claim 1, wherein the diaphragm is a resilient element.

5. The delivery device of claim 1, further comprising a nosepiece configured to fit in a nostril of the subject through which a substance is delivered to a nasal airway of the subject.

6. The delivery device of claim 5, wherein the nosepiece is in fluid communication with the air channel, and an air flow, when delivered through the air channel, acts to entrain the substance.

7. The delivery device of claim 1, in which the mouthpiece is configured to be gripped in a mouth of the subject.

8. The delivery device of claim 7, in which the mouthpiece is configured to be gripped by the subject's teeth.

9. A delivery device comprising:
   a mouthpiece adapted for a subject to exhale through;
   a channel which is in fluid communication with the mouthpiece;
   a delivery unit;
   a flexible diaphragm which is disposed in the channel, the diaphragm restricting gas flow through, the channel until pressure in the mouthpiece equals or exceeds a predetermined actuation pressure; and
   a rupturing element for rupturing the diaphragm when the pressure in the mouthpiece equals or exceeds the predetermined actuation pressure.

10. The delivery device of claim 9, in which the delivery unit is configured to deliver a metered dose of a substance.

11. The delivery device of claim 10, where the substance is a liquid.

12. The delivery device of claim 10, where the substance is a powder.

13. A delivery device comprising:
    a nosepiece;
    a mouthpiece adapted for a subject to exhale through;
    a channel which is disposed downstream of the mouthpiece and upstream of the nosepiece;
    a delivery unit;
    a flexible diaphragm which is disposed in the channel, the diaphragm restricting gas flow through the channel until pressure in the mouthpiece equals or exceeds a predetermined actuation pressure; and
    a rupturing element for rupturing the diaphragm when the pressure in the mouthpiece equals or exceeds the predetermined actuation pressure.

14. The delivery device of claim 13, wherein the delivery unit is configured to deliver a metered dose of a substance.

15. The delivery device of claim 14, in which the substance is a liquid.

16. The delivery device of claim 14, in which the substance is a powder.

17. The delivery device of claim 13, further comprising a housing.

18. The delivery device of claim 13, in which the mouthpiece is proximate to an inlet of the channel.

* * * * *